United States Patent [19]

Yamada et al.

[11] Patent Number: 4,925,609
[45] Date of Patent: May 15, 1990

[54] OXYGEN-SENSING ELEMENT

[75] Inventors: Hisao Yamada, Orange; Thomas Yuan, North Randall, both of Ohio

[73] Assignee: Stemcor Corporation, Cleveland, Ohio

[21] Appl. No.: 182,547

[22] Filed: Apr. 18, 1988

Related U.S. Application Data

[62] Division of Ser. No. 20,446, Mar. 2, 1987, Pat. No. 4,740,288.

[51] Int. Cl.⁵ ............................................. C04B 33/32
[52] U.S. Cl. ........................................ 264/61; 264/63
[58] Field of Search ............... 204/412, 424, 425, 427, 204/; 264/61, 63

[56] References Cited

U.S. PATENT DOCUMENTS

| | | | |
|---|---|---|---|
| 3,598,711 | 8/1971 | Flais | 204/427 |
| 4,193,857 | 3/1980 | Bannister et al. | 264/61 |
| 4,302,312 | 11/1981 | Ishitani et al. | 204/195 |
| 4,391,691 | 7/1983 | Linder et al. | 204/426 |
| 4,487,680 | 12/1984 | Logothetis et al. | 204/425 |
| 4,496,455 | 1/1985 | Linder et al. | 204/425 |
| 4,570,479 | 2/1986 | Sakurai et al. | 204/426 |
| 4,798,693 | 1/1989 | Mase et al. | 264/61 |

OTHER PUBLICATIONS

Vassell et al., Extended Range Air-to-Fuel Ration Sensor, SAE Tech. Paper, Apr. 25, 1984.
Soejima et al., Multi-Layered Zirconia Oxygen Sensor for Lean Burn Engine Application, SAE Tech. Paper, 850378 (1985).
Kamo et al., Lean Mixture Sensor, SAE Tech. Paper 85038 (1985).
Ueno et al., Wide-Range Air Fuel Ratio Sensor, SAE Tech. Paper 860409 (1986).
Suzuki et al., Air-Fuel Ratio Sensor for Rich, Stoichimetric and Lean Ranges, SAE Tech. Paper 860408 (1986).
Suzuki et al. Thick-Film Zirconia Air-Fuel Ratio Sensor with a Heater, etc., SAE Paper 850379 (1985).

Primary Examiner—James Derrington
Attorney, Agent, or Firm—Joseph G. Curatolo; Jeffrey A. Wyand; Larry W. Evans

[57] ABSTRACT

An oxygen-sensing element particularly for use in the exhaust stream of an internal combustion engine. In one embodiment, the sensing element may be a tubular solid electrolyte body with a transverse web forming a relatively shallow recess at one end of the body and a relatively deep tube at the other. Separate electrodes are formed on the surface of the body proximate the recess and on both opposing sides of the web. A porous plug disposed in the recess covers one of the electrodes. When the electrode on the surface of the body is exposed to the exhaust stream of a fuel-rich air-fuel mixture, the EMF across that electrode and the electrode on the underside of the web, which is exposed to fresh air, is indicative of the oxygen content of the exhaust stream. When an exhaust stream from a fuel-lean air-fuel mixture is present, the magnitude of an oxygen pumping current that flows between the electrodes disposed on opposing sides of the web, in response to a voltage applied across those electrodes, indicates the oxygen content of the exhaust stream.

The sensing element body may be conveniently formed from a slip prepared by ball milling yttria-stabilized zirconia powder with water and a binder. The slip may be cast in a mold or dried to form a flowable powder that is molded under pressure to form a green body. After calcining of the green body, electrodes are formed on the body by applying a platinum paste and heating it. A slurry of ball-milled calcined yttria-stabilized zirconia powder is disposed in the recess. The calcined green body and slurry are fired to produce a sensing element in which a tightly fitting porous plug, free of cracks and shrinkage away from the body, is disposed in the recess.

16 Claims, 3 Drawing Sheets

OXYGEN-SENSING ELEMENT

This is a division of co-pending application Ser. No. 20,446 filed Mar. 2, 1987, now U.S. Pat. No. 4,740,288 issued Apr. 26, 1988.

BACKGROUND

This invention relates to elements for sensing the oxygen content of a gaseous mixture, particularly the oxygen content of the exhaust stream from an internal combustion engine. More particularly, the invention relates to an oxygen-sensing element that is effective in measuring the oxygen content in exhaust mixtures resulting from the combustion of both fuel-rich and fuel-lean air-fuel mixtures. The sensing element can supply information to electronic control circuitry to control the content of an air-fuel mixture supplied to an internal combustion engine so that fuel consumption is minimized, pollutant emissions are limited and/or other goals are achieved.

Electronic controls responding to the oxygen content of the exhaust stream from internal combustion engines have been in use in production automobiles in the U.S. since about 1976. These controls assist automobile manufacturers in meeting pollution emission standards and fuel economy requirements. Most of the controls respond to information that is produced by a sensing element disposed in the exhaust stream. That element provides an electrical signal indicative of the oxygen content of the exhaust stream. When a so-called fuel-rich air-fuel mixture is supplied to an internal combustion gasoline engine, meaning there is an excess of fuel compared to the amount of oxygen available to burn the fuel, the exhaust stream contains little oxygen. When the air-fuel mixture is fuel-lean, there is an excess of air over that needed to burn the fuel, so the exhaust stream contains a relatively large amount of oxygen. At the point when the air-fuel mixture is precisely correct for complete combustion, i.e., the stoichiometric mixture, there is a transition in the oxygen content of the exhaust stream.

The oxygen-sensing elements most used and studied employ noble metal electrodes disposed on a zirconia body. In a device employing two opposed electrodes on a zirconia body with one of the electrodes exposed to a gaseous mixture containing a first oxygen content and the other electrode exposed to a gaseous mixture containing a different, second oxygen content, an EMF (electromotive force), i.e., the Nernst voltage, will appear across the electrodes. The magnitude of that EMF is related to the comparative oxygen contents, of the two mixtures, that is, to the comparative oxygen partial pressures of the two mixtures. If one of the mixtures is air, so that its oxygen content is known, the oxygen content of the other gas mixture can be determined.

Some of the known oxygen sensors employ the oxygen pumping phenomenon. Oxygen can be transported through solid electrolytes, like zirconia, when catalytic electrodes are disposed on the electrolyte. A voltage impressed across the electrodes will cause ionization of ambient oxygen at the negative polarity electrode. The oxygen ion will migrate through the electrolyte to the positive polarity electrode where the ion is neutralized and released from the catalytic electrode as an atomic or molecular species. That is, oxygen is transported or pumped under the influence of the electric field, from the vicinity of one electrode to the other. The volume of the oxygen pumped is measured by the electrical current flowing between the electrodes.

The Nernst voltage produced in a conventional oxygen sensor is proportional to the logarithm of the ratios of the oxygen partial pressures at the opposed electrodes. As a result, in a fuel-rich air-fuel mixture, meaning relatively low oxygen content in the exhaust stream, the Nernst voltage is relatively high, for example, hundreds of millivolts. However, for a fuel-lean air-fuel mixture, meaning increased oxygen content in the exhaust stream, the sensing element voltage decreases to less than about 100 millivolts. Moreover, the sensor sensitivity, i.e., the change in the sensor voltage in response to air-fuel variations in the fuel-lean mixtures, is relatively small. Thus it is difficult, with a conventional Nernst voltage sensor, to determine the air-fuel ratio from an exhaust stream produced from combusting a fuel-lean air-fuel mixture.

In order to achieve improved fuel economy, it is desirable to operate an internal combustion engine with a fuel-lean air-fuel mixture whenever possible, for example, when swift acceleration is not required. Since the conventional Nernst voltage sensor is ineffective in sensing the oxygen content in exhaust streams produced by combusting air-fuel mixtures in fuel-lean mixture range, considerable effort has been expended in devising an oxygen-sensing element that can provide, in response to fuel-lean mixture exhaust streams, an electrical signal that is both relatively large in its magnitude and its sensitivity. Some of the proposed devices are formed of multiple layers of refractory or ceramic materials that are fused together with glass frits. Some of the proposed devices employ multiple inlet apertures of different sizes that control the flow of gas mixtures into internal volumes where electrodes sense oxygen content. Still other oxygen-sensing elements include combinations of porous and non-porous layers of yttria-stabilized zirconia in combination with multiple electrodes. However, none of these sensing elements are simple to manufacture since they require careful registration and sealing of several thin ceramic layers or sequential, multiple depositions of zirconia and of metal electrodes. Accordingly, a need exists for an oxygen-sensing element that is simple to manufacture and therefore, relatively inexpensive, and that responds to the oxygen content of exhaust streams produced by combusting both fuel-rich and fuel-lean air-fuel mixtures with an electrical signal of relatively large magnitude and of sufficient sensitivity to discern small changes in mixture content.

SUMMARY OF THE INVENTION

Oxygen-sensing elements according to the invention include three electrodes, each disposed on a solid electrolyte body, one of the electrodes being covered by a porous plug. Preferably the covered electrode is disposed in a recess containing the porous plug. One of the electrodes is exposed to the gaseous mixture in which oxygen content is to be determined. Another of the electrodes is exposed to a reference mixture, such as air, containing a known amount of oxygen. The electrode covered by the porous plug is exposed, through the plug, to the mixture containing the unknown oxygen content.

In the presence of an exhaust stream produced from combustion of a fuel-rich air-fuel mixture, the electrodes directly contacting the exhaust stream and reference mixture are used as a conventional Nernst voltage sensor. In the presence of the exhaust produced from combustion of a fuel-lean air-fuel mixture, a voltage is applied across the reference electrode and the electrode covered by the porous plug. The oxygen pumping current that flows between those electrodes in response to the applied voltage indicates the oxygen content of the exhaust stream.

An embodiment of a sensing element body according to the invention is conveniently prepared from yttria-stabilized zirconia by milling its powder with water and a binder and, preferably, a dispersant and defoamer, to form a slip. The slip may be cast into a desired shape in a mold to form a green body. Alternatively, the slip may be spray dried to form a powder. The powder may be isostatically pressed to form a green body. In either case, the green body is calcined to give it handling strength. The body preferably includes a transverse web that forms, with the body, a shallow recess near one end of the body and an opposing, relatively deep tube. Any roughness at the recess end of the body is removed so that the body surface lies substantially in a plane. Electrodes are formed by applying a metal bearing paste and baking it to consolidate the metal. In order to match coefficients of thermal expansion, the porous plug is formed from a ceramic powder, preferably the same yttria-stabilized zirconia powder used in the body. But the powder is not milled until it has been calcined. The calcined powder is milled with a liquid. The product is dried and then mixed with other ingredients to form a slurry. The slurry is deposited in and above the recess with the aid of a temporary collar applied to the body. After the slurry dries, the excess is scraped off and the body and plug are fired. The plug fits tightly in the recess and is free of slump, cracks and shrinkage from the body as manufactured and in use.

DETAILED DESCRIPTION OF THE PREFERRED EMBODIMENTS

Figure 1:
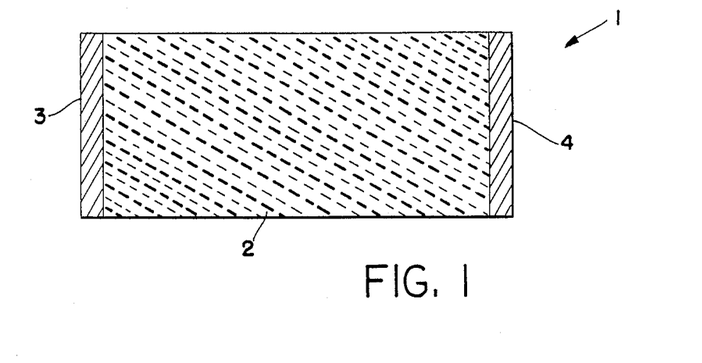
FIG. 1 is a schematic, sectional view of a conventional Nernst voltage oxygen-sensing element.

A conventional Nernst voltage oxygen-sensing element 1 is shown in a schematic cross-sectional view in FIG. 1. The sensor includes a body 2 formed of a solid electrolyte. Body 2 is referred to as a solid electrolyte because it is formed of a material that can conduct a current of oxygen ions under the influence of an external voltage that is applied to the body, i.e., the oxygen pumping phenomenon referred to above. In the absence of an external voltage, an oxygen current can attempt to flow in response to an oxygen concentration gradient across the body resulting in the production of an EMF across the body. Such solid electrolyte materials are well known and a preferred solid electrolyte material is zirconia, particularly zirconia containing a relatively small amount of yttria as a stabilizer. Other solid electrolytes, such as ceria ($CeO_2$), and other stabilizers, such as oxides of calcium and magnesium, are known, but yttria-stabilized zirconia is a preferred solid electrolyte material for Nernst voltage oxygen sensors.

Electrodes 3 and 4 are disposed on opposed surfaces of body 2. Electrodes 3 and 4 are preferably formed of a noble metal, such as platinum, palladium or rhodium, that catalyzes chemical reactions with oxygen at their surfaces. Platinum is the preferred metal. In general, the electrodes are thin and porous, allowing oxygen to reach body 2 while still contacting the catalyzing metal electrode. Oxygen can thus be ionized or ionic oxygen can be reduced at the electrodes.

Electrodes 3 and 4 are immersed in gas mixtures that are isolated from each other (by a separator that is not shown) and that may contain different amounts of oxygen. A difference in the oxygen concentration in each mixture, i.e., at each electrode, causes a migration of oxygen ions through body 2, producing an EMF across electrodes 3 and 4 that builds until it is sufficient to counteract the oxygen flow. When that equilibrium is reached, the voltage produced, the so-called Nernst voltage, is well known to be $$V_{3-4} = [RT/4F][ln(P_{O3}/P_{O4})] \quad (1)$$

where
R = the gas constant,
T = absolute temperature,
F = Faraday's constant, and
$P_{O3}, P_{O4}$ = the partial pressure of oxygen at electrodes 3 and 4, respectively.

Figure 2:
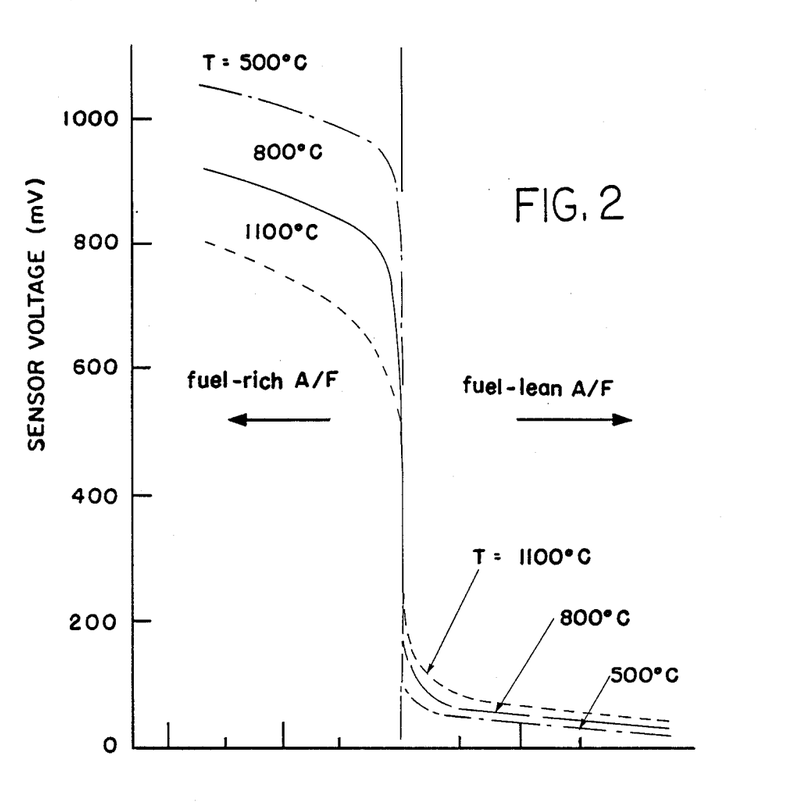
FIG. 2 is a graphical representation of the typical response of a conventional Nernst voltage oxygen-sensing element.

When sensing element 1 is used in the exhaust stream of an internal combustion engine, the Nernst voltage generated swings widely depending on the air-fuel mixture supplied to the engine. Assuming electrode 4 is exposed to fresh air which has a relatively stable, known oxygen content and electrode 3 is exposed to the exhaust stream, once the voltage across the electrodes is measured, the oxygen content of the exhaust stream may be calculated. However, because of the logarithmic factor in Equation 1, the response is strongly nonlinear, as illustrated in FIG. 2. When the air-fuel mixture is rich in fuel, little oxygen is left in the exhaust stream, the oxygen partial pressures at electrodes 3 and 4 are significantly different and a relatively large voltage is produced. However, when the air-fuel mixture is lean in fuel, much more oxygen appears in the exhaust stream and the argument of the logarithm in Equation 1 more closely approaches unity, meaning the voltage produced decreases significantly. In addition, when the costituents of a fuel-lean mixture are changed, the amount of leftover oxygen in the exhaust does not change significantly. Therefore, the response of sensing element 1 to a fuel-lean air-fuel mixture is small and the sensitivity of the response over a wide range of fuel-lean mixtures is poor. Moreover, unlike the response in the fuel-rich region, the lean mixture response is relatively insensitive to variations in the temperature of sensing element 1.

Figure 3A:
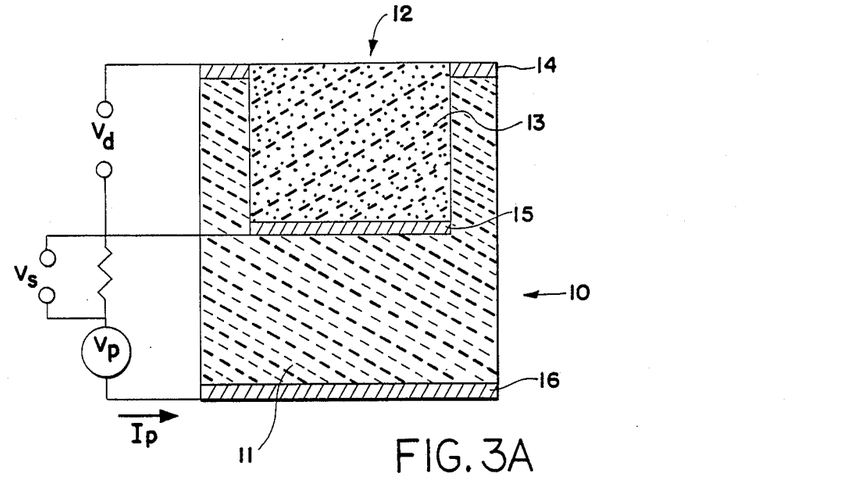
FIGS. 3A and 3B are, respectively, schematic and representational sectional views of an embodiment of an oxygen-sensing element according to the invention.
Figure 3B:
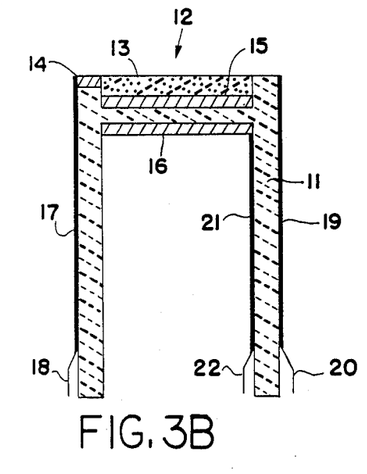
Figure 4:
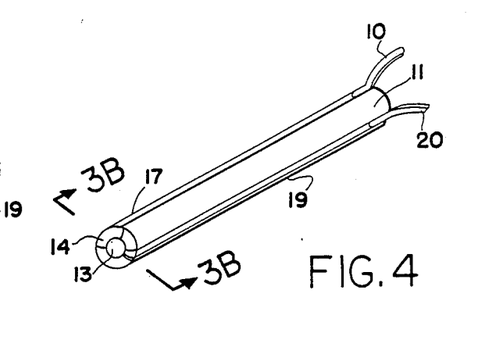
FIG. 4 is a perspective view of an embodiment of an oxygen-sensing element according to the invention.

An embodiment of a novel oxygen-sensing element 10 that provides the desirable response of element 1 to the exhaust from a fuel-rich air-fuel mixture and equally good response to the exhaust from a fuel-lean air-fuel mixture is shown in cross-section, schematically in FIG. 3A, and representationally in FIGS. 3B and 4. Like elements in these figures are given the same reference numbers. None of the drawings is drawn to any scale. Element 10 includes a body 11 formed of a solid electrolyte that has a recess 12 at one end. Recess 12 is filled with a porous plug 13. Plug 13 is a ceramic material and is preferably composed of the same or nearly the same solid electrolyte material as body 11, so that the thermal coefficients of expansion of the plug and body are the same or nearly the same. An electrode 14 is disposed on the end of body 11 adjacent recess 12. A second electrode 15 is disposed at the bottom of recess 12 and is covered by porous plug 13. A third electrode 16 is disposed underneath recess 12 opposite electrode 15. By a comparison of FIGS. 3A and 3B to FIG. 1, it is readily seen that element 10 includes a conventional Nernst oxygen-sensing element comprising electrodes 14 and 16 separated by body 11. Thus element 10 can function just as element 1 to sense the oxygen content of an exhaust stream produced by combusting a fuel-rich air-fuel mixture. The gaseous mixtures that contact each of electrodes 14 and 16 are different and are isolated from each other by a seal, gasket or mounting fixture (not shown) that prevents the mixtures from intermixing with each other. Electrode 16 is exposed to a reference gaseous mixture, such as fresh air, having a known oxygen content, while electrode 14 is exposed to the gaseous mixture, such as an exhaust stream, in which the oxygen content is to be determined. The EMF developed across electrodes 14 and 16 and the known oxygen partial pressure at electrode 16 are used with Equation 1 to determine the oxygen pressure in the gaseous mixture in contact with electrode 14.

Adapting Equation 1 to the embodiment of FIG. 3A, $$V_{14-16} = [RT/4F][\ln(P_{O14}/P_{O16})]$$

or $$P_{O14} = P_{O16} e^{(4F V_{14-16}/RT)}$$

where $P_{O14}$, $P_{O16}$ = partial pressure of oxygen at electrodes 14 and 16, respectively; and $V_{14-16}$ = the EMF across electrodes 14 and 16.

With respect to FIG. 3A, $V_{14-16}$ is shown as $V_d + V_p$, and $I_p$ and $V_s$ are both zero.

The gaseous mixture in contact with plug 13 diffuses through the plug to electrode 15. When an equilibrium is established, the concentration of oxygen at electrode 15 is the same as that at the outside surface of plug 13. However, when the oxygen concentration at electrode 15 is different from that at the outside surface of plug 13, the concentration gradient causes diffusion of oxygen to or from electrode 15 through porous plug 13 As is well known, if the negative terminal of a voltage source is applied to electrode 15 and its positive terminal is applied to electrode 16, oxygen molecules at electrode 15 will be ionized. The ions will flow through body 11 to electrode 16 where the extra electrons will be removed, forming free oxygen atoms or molecules again. This well known oxygen pumping phenomenon results in a current flow, the so-called pumping current, $I_p$, from electrode 15 to electrode 16. As oxygen is removed from the bottom of recess 12 adjacent electrode 15 by oxygen pumping, the resulting concentration gradient across plug 13 causes more oxygen to diffuse through the plug. But the resistance of plug 13 to the influx of oxygen, i.e., the upper limit on the diffusion rate, means that eventually an equilibrium oxygen concentration will be established at electrode 15. That is, the influx of oxygen will reach a constant value that is limited by the diffusion characteristics of plug 13 and the oxygen concentration at electrode 14. At that equilbrium, the pumping current will reach a constant value for a given voltage applied across electrodes 15 and 16. Since the only variable factor in determining this equilibrium pumping current, when a constant voltage is applied across electrodes 15 and 16, is the oxygen concentration at electrode 14 (the diffusion characteristics of a particular plug being invariant and assuming the oxygen content of the reference gas mixture is constant), the oxygen content of the gas mixture at electrode 14 can be determined by measuring the pumping current. The relationship between the pumping current and the oxygen partial pressure in the gas mixture at electrode 14 is $$I_{p16-15} = P_{O14}[4FD/x][1 - e^{-(4FV_{14-15}/RT)}] \quad (2)$$

where the terms not previously defined are:

$I_{p16-15}$ = the electrical current flowing from electrode 16 to electrode 15;

x = distance between electrode 14 and electrode 15, i.e., the length oxygen has to diffuse through plug 13 to reach electrode 15;

D = the diffusion constant for oxygen through plug 13; and $V_{14-15}$ = the voltage that appears across electrodes 14 and 15 because of the oxygen partial pressure gradient between them.

The only variables in Equation 2 for a given sensing element are $P_{O14}$ and $V_{14-15}$. When $V_{14-15}$ is about 0.2 volts or larger, the exponential term in Equation 1 is much less than one and the oxygen pumping current is essentially directly proportional to the oxygen partial pressure in the exhaust stream. In terms of the symbols of FIG. 3A, $V_{14-15}$ equals $V_d$ and $I_{p16-15}$ is the same as $I_p$. A voltaic measure of $I_p$ is produced by connecting a resistor, of a value that does not significantly change $I_p$, in series with voltage generator $V_p$, to produce a voltage signal, $V_s$, that is proportional to $I_p$.

In order to complete sensor 10, means must be provided for establishing electrical communication with the electrodes as indicated in FIG. 3B. As described below, electrodes 14, 15 and 16 are preferably platinum formed by applying a metal-bearing paste to body 11 in which the metal is consolidated by heating and driving off the binder in the paste. Electrode 14 is formed on a portion of body 11 and a stripe of the metal paste is applied along a side of body 11 to form a conductor 17. Proximate the end of conductor 17 opposite electrode 14, a metal ribbon 18 is attached to conductor 17 with another metal-bearing paste or other electrically conducting adhesive, by spot-welding or some other conventional technique. Ribbon 18 may be a wire or flat ribbon of any metal or alloy that bonds well to strip 17 and can withstand the heat to which element 10 is subjected. In like fashion, a stripe 19 of an electrical conductor from electrode 15 is disposed between plug 13 and an internal recess wall of body 11, over the end of body 11 and down its side. Another ribbon 20 is attached to stripe 19 for establishing electrical communication to electrode 15. A stripe 21 contacting electrode 16 within body 11 is disposed on the inside wall of body 11 and is contacted near the end of the body by a ribbon 22.

The preferred embodiment of sensing element 10 shown in FIG. 4 is circular in cross-section, but the invention is not so limited. A tubular body is preferred so that a reference gas mixture can contact a reference electrode, such as electrode 16, yet be isolated easily from the other electrodes. Likewise, a recess formed by a web disposed transverse to the body is preferred so that all oxygen molecules diffusing through the porous plug are presented with a substantially uniform path length to reach the electrode disposed beneath the plug. However, other embodiments of the invention may be constructed with a recess having a different structure or without a recess so that diffusion paths of different lengths between the gas mixture being sensed and the electrode covered by the porous material exist. An example of such a construction appears in a schematic, sectional view in FIG. 5. There, a sensing element 50 includes a first solid electrolyte body 51 having opposed first and second surfaces 52 and 53. While surfaces 52 and 53 are, for simplicity, shown in FIG. 5 as planar, parallel surfaces, this schematic drawing is not intended to be limiting. Electrodes 54 and 55 are disposed on surface 52. An electrode 56 is disposed on surface 53 opposite electrode 55. A relatively porous body 57 is disposed on surface 52 covering electrode 55. This embodiment of the invention functions in the same way as sensor 10 and so repetition of the explanation of the operation is not needed. Electrodes 54, 55 and 56 correspond to electrodes 14, 15 and 16, respectively. Body 57 corresponds to plug 13. Equation 2 applies to element 50. Preferably, the edges of electrode 55 beneath porous layer 57 are widely spaced from the edges of layer 57, relative to the depth of the layer 57, so that relatively little of the diffusing oxygen reaches electrode 55 along its edges. In that case, x in Equation 2 is the distance from electrode 55 to the surface of body 57 opposite body 51.

It is understood by those of skill in the art that the bodies (e.g., 11 and 51) of the novel sensing element are non-porous, but an oxygen concentration gradient across them can produce a Nernst voltage and ionized oxygen can flow through them. By contrast, significant amounts of unionized molecules diffuse through the porous plug or layer (e.g., 13 or 57) in response to a concentration gradient across them. The molecular, diffusive flow is to be distinguished from the ionic oxygen drift current through the relatively non-porous body in response to a concentration gradient that produces the Nernst voltage.

Returning to the embodiment of FIGS. 3B and 4, recess 12 is formed by a web 23 that lies transverse to the central axis of body 11. The depth of recess 12 is shallow compared to the depth of the opposing tube including electrode 16. As seen in FIG. 4, electrode 14 occupies only a part of the surface of body 11 that is proximate recess 12. That surface, which is annular in embodiment 10, preferably lies substantially in a plane. Part of that annular surface is occupied by the stripe 19 that enables electrical communication with electrode 15. However, it is preferred that the area of electrode 14 on the annular surface be larger than the area on that surface that is occupied by stripe 19.

Figure 6:
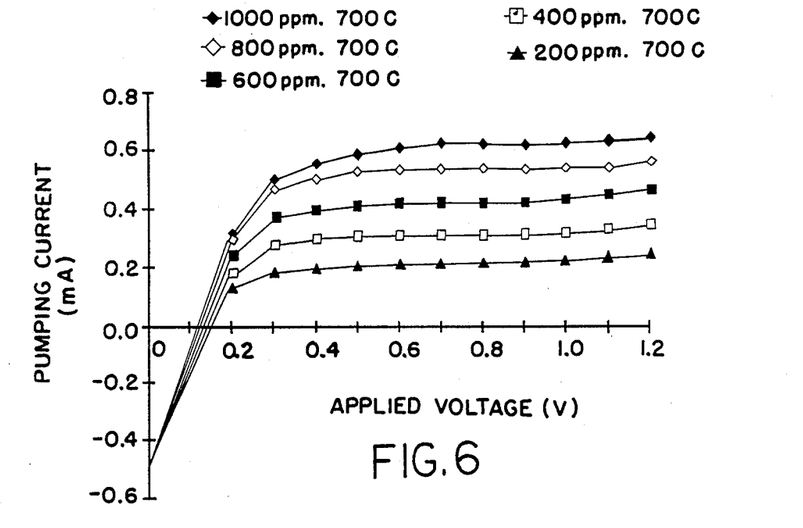
FIG. 6 is a graphical representation of the measured response of an embodiment of the invention, as a function of applied pumping voltage, to gas mixtures containing relatively large amounts of oxygen.
Figure 7:
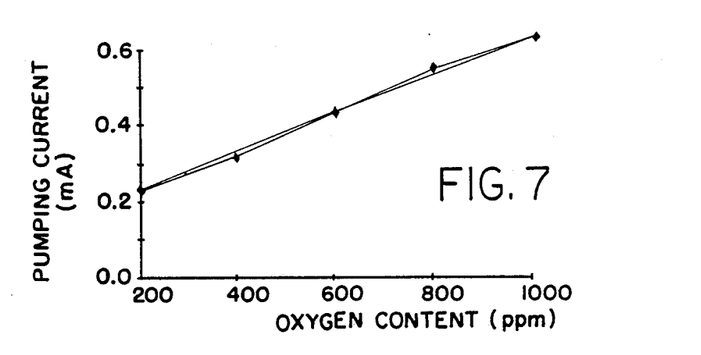
FIG. 7 is a graphical representation of the measured response of an embodiment of the invention, when a constant pumping voltage is applied, to gas mixtures containing relatively large amounts of oxygen.

Embodiments of the invention similar to that shown in FIG. 4 have been prepared by the process described below and their electrical responses have been measured. Measured results are shown in FIGS. 6 and 7. An oxygen-sensing element according to the invention was heated to a temperature (600° to 800° C.) typically found in the exhaust stream produced by an internal combustion engine. At that temperature, gas mixtures containing various known oxygen concentrations corresponding to the exhaust stream mixtures produced by the combustion of fuel-lean air-fuel mixtures were passed over the heated sensing element and the equilibrium oxygen pumping currents were measured. The measured pumping currents are plotted on the ordinate in FIG. 6 versus the voltage applied to the pumping electrodes, which is plotted on the abscissa. A curve is plotted for each gas mixture. For low voltages, the pumping current declines to zero; for intermediate voltages, the pumping current is substantially independent of applied voltage; and at voltages exceeding about 1.1 volts, other effects, such as electrical breakdown of the body, appear to produce some increases in current with applied voltage. FIG. 7 illustrates the measured response of the novel sensing element in terms of pumping current, plotted on the ordinate, versus the oxygen content being sensed, plotted on the abscissa. These results are plotted for a fixed, intermediate pumping voltage (0.7 volts) and show that the desired linear relationship between current and oxygen concentration in the exhaust stream is achieved.

Figure 8:
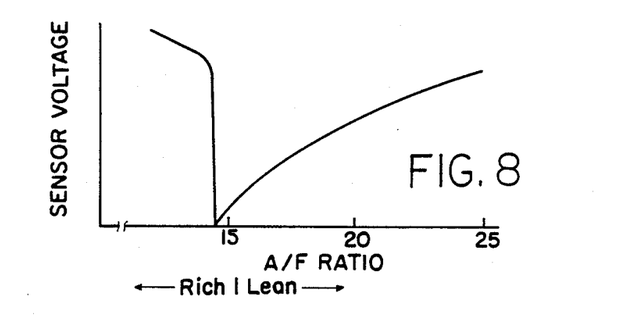
FIG. 8 is a graphical representation of the response of an embodiment of the invention to exhaust gases produced by combustion of various fuel-rich and fuel-lean air-fuel mixtures.

The complete response of an oxygen-sensing element according to the invention is diagrammed in FIG. 8. For exhaust streams produced from the combustion of mixtures in the fuel-rich air-fuel mixture region, the conventional Nernst response is shown. A relatively large electrical signal is generated that decreases rapidly to zero as a stoichiometric mixture (about 14.7 parts of air to one part fuel) is reached. Beyond that point, the sensing element responds as shown in FIGS. 6 and 7 with a nearly linear signal increase in response to increasing oxygen in the exhaust stream. To take advantage of this response, it is necessary to switch the sensing electrodes being used and to energize or de-energize the pumping current as the mixture passes through the stoichiometric point in FIG. 8. Alternatively, the Nernst EMF and the pumping current can be measured sequentially and repetitively. The detected sequential signals are electronically processed to determine the air-fuel mixture region, i.e., which section of the FIG. 8 characteristic is applicable. Thereafter, that section of the characteristic is employed to determine the oxygen content.

While application of the novel sensing element to vehicular engines has been emphasized, it is obvious that other applications can be made. The novel sensor can be of use in control systems for furnaces, boilers and other apparatus in which a hydrocarbon fuel is combusted.

In sensing element according to the invention, it is very important that the porous plug or layer be free of cracks or voids and that it adhere tightly to the solid electrolyte body of the element. Cracks, voids or separations of the porous material from the electrolyte body could admit oxygen molecules directly to the electrode that is intended to be covered by the porous solid electrolyte. If direct access were possible, Equation 2 would not describe the sensing element response. Considering the relatively high temperatures at which sensing elements according to the invention are intended to operate, it is important that the porous plug and solid electrolyte bodies have the same or nearly the same coefficients of thermal expansion. This goal may be achieved by making the plug and body of the same material. An exemplary process for making an embodiment of the invention having a porous plug and an electrolyte body is described below.

Yttria-stabilized zirconia is the preferred solid electrolyte. Yttria-stabilized zirconia powder is available from a number of commercial suppliers. A suitable powder is available from Daiichi Kigenso of Osaka, Japan with the designation NEY-5M. Green bodies can be prepared from yttria-stabilized zirconia by slip casting or isostatic pressing.

In order to cast a solid electrolyte body a slip is made by mixing and milling zirconia powder with a binder and water in a ball mill. It is preferred that a dispersing agent and a defoaming agent be added to the mix to prevent agglomeration of the powder particles and to avoid excessive foaming, respectively. In a recipe that gives good results, 150 grams of yttria-stabilized zirconia powder is milled with 0.5 gram of pyrrolidone as a binder, 50 cubic centimeters of water and two drops each of ammonium acrylate (sold as Darvan C by R. T. Vanderbilt Company, Inc.) as a dispersant and tributyl phosphate as a defoamer. These ingredients are mixed and milled for a sufficiently long period, e.g., four to eight hours, so that a uniform slip is obtained. Preferably, excess air is removed from the slip after the mixing and milling process with a vacuum. The slip is then cast into a mold, preferably plaster, that has been prepared to produce the desired body shape. The slip casting process is a conventional ceramic process step in which excess slip is poured from the mold once the body wall has formed. After the green body has dried, it is removed from the mold.

In the isostatic process, the slip is spray dried to form a flowing powder. The powder is poured into a mold and isostatic pressure is applied to press the powder into a green body of the desired shape. The pressed green body can be removed from the mold without waiting for a slip to dry and harden.

Regardless of the forming process, the green body is calcined to give it sufficient strength to withstand handling. It is important that the calcining process be carried out at 1000° to 1100° C. for about four to eight hours for the resulting intermediate product to produce the desired final product when the additional processing steps described below are used.

Figure 5:
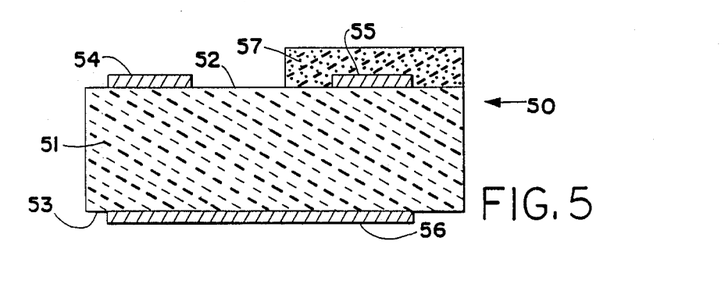
FIG. 5 is a schematic, sectional view of an embodiment of an oxygen-sensing element according to the invention.

The calcined body is strong enough for smoothing and for the application of electrodes. When an embodiment of the invention like that shown in FIGS. 4 and 5 is being made, surfaces may have to be ground flat. After calcining, the body has sufficient strength to permit grinding or abrading, as necessary, to flatten surfaces. The annular end surface of an embodiment like that shown in FIG. 4 may be ground flat and any mold seams may be smoothed with ordinary abrasive paper. After any necessary flattening and/or smoothing, electrodes are applied. Electrodes are applied as a metal bearing paste, the metal preferably being platinum or some other noble metal that catalyzes oxygen reactions and can withstand the temperatures at which the sensing element will operate. Typical metal bearing pastes are available from Engelhard Corporation. The paste is applied by painting, screen-printing or another conventional technique to define the three electrodes and conducting stripes for contacting the electrodes. To drive off the binder from the paste and consolidate the metal, the calcined body is heated again. The temperature of the metal consolidation step should not exceed the temperature of the previous calcining step, but should be sufficient to form a bond between the body and consolidated metal. A temperature of approximately 900° to 1050° C. is sufficient to form the desired platinum to ceramic bond.

The material for a porous plug or layer may be separately formed from a ceramic powder, preferably another quantity of the same yttria-stabilized zirconia powder used to form the body. In order to prepare a porous material, i.e., containing large enough interstices for diffusion of oxygen through it, the powder is first calcined to form enlarged consolidated porous masses. Careful control of this calcining process is particularly important to successful fabrication of sensing elements according to the invention. Calcining at approximately 1100° to 1300°°C. for about two to four hours provides a useful product. This calcined powder product is milled in a ball mill with a liquid for about four to eight hours. The liquid is preferably an organic solvent, such as ethanol, that is easily driven off with heat in a later step, but water or any other liquid that may be conveniently removed from the slurry can also be used. An appropriate mixture for milling is 100 grams of calcined powder in 200 cubic centimeters of ethanol or distilled water. The milled powder is dried and then mixed with other ingredients to form a slurry. The slurry may conveniently employ the same recipe already described for the zirconia slip.

It is important to control the surface contour of the porous plug or layer being formed. If a body with a recess is formed and the slurry for the porous member is poured into the recess and dried, the slurry will slump in drying. That is, the dried slurry will have a concave surface and a plug that has a non-uniform thickness will be formed. With a tubular body containing a recess, it is convenient to form a temporary collar or tube that projects beyond the recess end of the body. The recess is then slightly overfilled with the slurry, the excess being retained by the collar. The slurry is dried, preferably at a relatively low, elevated temperature such as 30° to 80° C., the collar is removed and any excess dried slurry is scraped from the end of the body without damaging the electrodes or their connecting stripes. When the slurry is used to form a porous layer, a similar temporary form or forms may be used to ensure formation of a substantially planar or other desired shape surface.

Once the slurry has been dried and shaped as desired, the slurry and calcined body assembly is fired. Firing hardens both the relatively non-porous body and the porous plug or body. This co-firing process may be effectively performed at approximately 1400° to 1600° C. for about two hours.

The processing steps described above involve a number of high temperature steps. It has been found that the temperatures and times of these steps must be carefully coordinated to produce embodiments of the element according to the invention. The foregoing process description is one set of such coordinated steps. In embodiments employing recesses, the processing described produces a porous plug of substantially uniform thickness that is free of cracks, voids and fissures and that does not separate from the main body of the element after repeated heating and cooling cycles. Likewise, since the coefficient of thermal expansion of the porous material is carefully matched to that of the solid electrolyte body, embodiments of the invention without recesses can withstand repeated thermal cycling without separation of porous components from the sensor body or cracking of the porous component.

A porous body might be formed by a process different from that described. For example, if a portion of a solid electrolyte body could be subjected to a treatment producing pores, then the entire body could be formed from solid electrolyte. Thereafter, the portion of the solid electrolyte disposed on an electrode would be treated so as to become porous.

The invention has been described with respect to certain preferred embodiments. Various modifications and additions within the spirit of the invention will occur to those of skill in the art. Therefore, the scope of the invention is limited solely by the following claims.

We claim:

1. A method of making a sensing element for producing an electrical signal indicative of the oxygen content of a combusted air-fuel mixture comprising:
   milling a mixture including a solid electrolyte powder, water and a binder to form a slip;
   forming from said slip a green body having first and second opposed surfaces;
   calcining said green body;
   applying first, second and third metal electrodes to said calcined green body, said second electrode being disposed on said first surface, said third electrode being disposed on said second surface opposite said second electrode;
   calcining a ceramic powder;
   milling said calcined powder in a liquid;
   forming a slurry with said milled, calcined powder;
   disposing said slurry on said first surface covering said second electrode; and
   firing said calcined green body and slurry to form a solid electrolyte body bearing a porous body covering said second electrode.

2. The method of claim 1 wherein said green body is formed by casting said slip in a mold.

3. The method of claim 1 wherein said green body is formed by spray drying said slip to form a flowable powder, casting said powder in a mold and applying pressure to said powder.

4. The method of claim 1 wherein said solid electrolyte powder comprises yttria-stabilized zirconia.

5. The method of claim 1 including milling said mixture in a ball mill for about four to eight hours.

6. The method of claim 1 wherein said green body is calcined at approximately 1000° to 1100° C. for about four to eight hours.

7. The method of claim 1 including applying metal electrodes to said calcined green body by applying a metal bearing paste to said calcined green body and heating said calcined green body to consolidate said metal into electrodes.

8. The method of claim 1 wherein said ceramic powder comprises yttriastabilized zirconia.

9. The method of claim 11 including calcining said ceramic powder at approximately 1100° to 1300° C. for about two to four hours.

10. The method of claim 1 including milling said calcined ceramic powder in a ball mill for about four to eight hours.

11. The method of claim 1 including drying said milled, calcined powder and forming a slurry by adding water and a binder to said dried powder.

12. The method of claim 11 wherein said body is tubular and includes a transverse web defining a recess and having said first and second surfaces, including disposing said slurry in said recess.

13. The method of claim 12 including disposing said first electrode proximate said recess.

14. The method of claim 12 including placing a collar around said calcined green body proximate said recess before disposing said slurry in said recess to retain any excess slurry.

15. The method of claim 14 including drying said slurry and removing said collar before firing.

16. The method of claim 15 including removing any of said dried slurry projecting beyond said recess before firing.

* * * * *

UNITED STATES PATENT AND TRADEMARK OFFICE
CERTIFICATE OF CORRECTION

PATENT NO.  : 4,925,609
DATED       : May 15, 1990
INVENTOR(S) : H. Yamada; Thomas Yuan It is certified that error appears in the above-identified patent and that said Letters Patent is hereby corrected as shown below:

Column 12, line 20, "yttriastabilized" should be -- yttria-stabilized --.

Column 12, line 30, insert the word "green" between the words "said" and "body".

Signed and Sealed this

Eighteenth Day of June, 1991

Attest:

HARRY F. MANBECK, JR.

*Attesting Officer*      *Commissioner of Patents and Trademarks*